US007560479B2

(12) United States Patent
Mehta et al.

(10) Patent No.: US 7,560,479 B2
(45) Date of Patent: *Jul. 14, 2009

(54) 3,6-DISUBSTITUTED AZABICYCLO HEXANE DERIVATIVES AS MUSCARINIC RECEPTOR ANTAGONISTS

(75) Inventors: Anita Mehta, Buffalo Grove, IL (US); Bruhaspathy Miriyala, Oxford, MS (US); Arundutt Viswanatham Silamkoti, Secunderabad (IN); Jang Bahadar Gupta, Kobe (JP)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/552,502

(22) PCT Filed: Apr. 10, 2003

(86) PCT No.: PCT/IB03/01327

§ 371 (c)(1),
(2), (4) Date: Feb. 12, 2007

(87) PCT Pub. No.: WO2004/089899

PCT Pub. Date: Oct. 21, 2004

(65) Prior Publication Data

US 2007/0135508 A1 Jun. 14, 2007

(51) Int. Cl.
*A61K 31/403* (2006.01)
*C07D 209/52* (2006.01)
(52) U.S. Cl. .................................. 514/412; 548/515
(58) Field of Classification Search ................. 514/412; 548/515

See application file for complete search history.

(56) References Cited

U.S. PATENT DOCUMENTS

| 3,176,019 | A | 3/1965 | Campbell et al. | ........ 260/293.4 |
| 5,281,601 | A | 1/1994 | Cross et al. | ................. 514/320 |
| 5,948,792 | A | 9/1999 | Tsuchiya et al. | ............ 514/317 |
| 6,034,082 | A | 3/2000 | MacKenzie et al. | ...... 514/233.5 |
| 6,130,232 | A | 10/2000 | Mase et al. | ................. 514/318 |
| 6,174,900 | B1 | 1/2001 | Okada et al. | ................. 514/317 |

FOREIGN PATENT DOCUMENTS

| EP | 0 325 571 | 7/1989 |
| EP | 0 388 054 | 9/1990 |
| EP | 0 801 067 | 10/1997 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/05641 | 2/1998 |
| WO | WO 98/29402 | 7/1998 |

OTHER PUBLICATIONS

Wess et al. (Life Sciences 2003, 72, 2047-2054).*
O'Neill, M. (Drug Discovery Today Oct. 2005, 10(20), 1338).*
Michel et al. (Naunyn-Schmiedeberg's Arch Pharmacol 2006, 374, 79-85).*
Latifpour et al. (The Journal of Pharmacology and Experimental Therapeutics 1989, 249(1), 81-88).*
Carrier et al. (The Journal of Pharmacology and Experimental Therapeutics 1987, 242(2), 531-535).*
Ahren et al. (Diabetologia 1996, 39, 383-390).*
Abrams et al. (British Journal of Pharmacology 2006, 148, 565-578).*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous System", *Journal of Medicinal Chemistry*, 43(23):4333-4353 (2000).
Broadley and Kelly, "Muscarinic Receptor Agonists and Antagonists", *Molecules*, 6:142-193 (2001).
Birdsall et al., "Muscarinic receptors: it's a knockout", *Trends in Pharmacological Sciences*, 22(5):215-219 (2001).
de Groat and Yoshimura, "Pharmacology of the Lower Urinary Tract", *Annual Review of Pharmacology and Toxicology*, 41:691-721 (2001).
Steers, "The future direction of neuro-urology drug research", *Current Opinion in CPNS Investigational Drugs*, 2(3):268-282.
Chapple, "Muscarinic receptor antagonists in the treatment of overactive bladder", *Urology*, 55(Suppl. 5A):33-46 (2000).

(Continued)

*Primary Examiner*—Kamal A Saeed
*Assistant Examiner*—Jason M Nolan
(74) *Attorney, Agent, or Firm*—Jayadeep R. Deshmukh, Esq.; George E. Heibel, Esq.

(57) ABSTRACT

This invention relates to derivatives of 3,6-disubstituted azabicyclo hexanes. The compounds of this invention can function as muscarinic receptor antagonists and can be used for the treatment of various diseases of the respiratory, urinary and gastrointestinal systems mediated through muscarinic receptors.

13 Claims, No Drawings

OTHER PUBLICATIONS

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Sagara et al., "Cyclohexylmethylpiperidinyltriphenylpropioamide: A Selective Muscarinic M3 Antagonist Discriminating against the Other Receptor Subtypes", *Journal of Medicinal Chemistry*, 45:984-987 (2002).

Mitsuya et al, "A Potent, Long-Active, Orally Active (2R)-2-[(1R)-3,3-Difluorocyclopentyl]-2-hydroxy-2-phenylacetamide: A Novel Muscarinic $M_3$ Receptor Antagonist with High Selectivity for $M_3$ over $M_2$ Receptors", *Journal of Medicinal Chemistry*, 43(26):5017-5029 (2000).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inhibition constant (*KI*) and the concentration of inhibitor which causes 50 per cent inhibition (*I50*) of an enzymatic reaction", *Biochemical Pharmacology*, 22:3099-3108 (1973).

* cited by examiner

3,6-DISUBSTITUTED AZABICYCLO HEXANE DERIVATIVES AS MUSCARINIC RECEPTOR ANTAGONISTS

FIELD OF THE INVENTION

This invention relates to derivatives of 3,6-disubstituted azabicyclo hexanes.

The compounds of this invention can function as muscarinic receptor antagonists, and can be used for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527). A review in *Current Opinions in Chemical Biology*, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142.

N. J. M. Birdsall et. al. in *Trends in Pharmacological Sciences*, 2001; 22: 215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs* 2: 268, C. R. Chapple et. al. in *Urology*, 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; BP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides 3,6-disubstituted azabicyclo hexanes as muscarinic receptor antagonists and are useful as safe and effective therapeutic or prophylactic agents for the treatment of various diseases of the respiratory, urinary and gastrointestinal systems and process for the syntheses of the compounds.

The invention also provides pharmaceutical compositions containing the compounds, and which may also contain acceptable carriers, excipients or diluents which are useful for the treatment of various diseases of the respiratory, urinary and gastrointestinal systems.

The present invention also includes within its scope prodrugs of the compounds. In general, such prodrugs are functionalized derivatives of these compounds which readily get converted in vivo into the defined compounds. Conventional procedures for the selection and preparation of suitable prodrugs are known to the artisan of ordinary skill in the art.

The invention also includes the enantiomers, diastereomers, N-oxides, polymorphs, pharmaceutically acceptable salts and pharmaceutically acceptable solvates, esters and metabolites of these compounds having the same type of activity.

The invention further includes pharmaceutical compositions comprising the compounds of the present invention, their enantiomers, diastereomers, prodrugs, N-oxides, polymorphs, pharmaceutically acceptable salts, pharmaceutically acceptable solvates, esters or metabolites, in combination with a pharmaceutically acceptable carrier and optionally included excipients.

Other advantages of the invention will be set forth in the description which follows, and in part will be apparent from the description or may be learnt by the practice of the invention.

In accordance with one aspect of the present invention, there are provided compounds having the structure of Formula I:

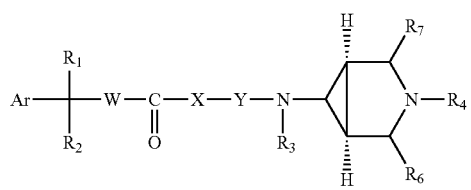

Formula I and their pharmaceutically acceptable salts, pharmaceutically acceptable solvates, esters, enantiomers, diastereomers, N-oxides, polymorphs, prodrugs, or metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhalo-alkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents alkyl, $C_3$-$C_7$ cycloalkyl ring which any 1-4 hydrogen atoms are substituted with halogen (e.g. F, Cl, Br, I), carbamoyl or lower alkyl;

W represents $(CH_2)_p$, where p represents 0 to 1;

X represents an oxygen, sulphur, NR or no atom wherein R represents hydrogen or $C_1$-$C_6$ alkyl;

Y represents $CHR_5CO$ wherein $R_5$ represents hydrogen, methyl or $(CH_2)q$ wherein q represents 0 to 4;

$R_3$ represents hydrogen, lower alkyl or $CO_2C(CH_3)_3$;

$R_6$ and $R_7$ are independently selected from H, lower alkyl, COOH, $CONH_2$, $NH_2$, or $CH_2NH_2$; and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$).

In accordance with a second aspect of the present invention, there are provided compounds having the structure of Formula II and their pharmaceutically acceptable salts, pharmaceutically acceptable solvates, esters, enantiomers, diastereomers, N-oxides, polymorphs, prodrugs, or metabolites wherein Ar, $R_1$, $R_2$, W, X, Y, $R_3$ and $R_4$ are as defined for Formula I.

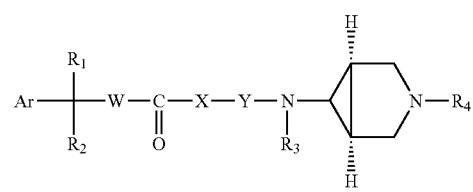

Formula II

In accordance with a third aspect of the present invention, there are provided compounds having the structure of Formula in and their pharmaceutically acceptable salts, pharmaceutically acceptable solvates, esters, enantiomers, diastereomers, N-oxides, polymorphs, prodrugs, metabolites, wherein Ar, $R_1$, $R_2$, $R_3$ and $R_4$ are as defined for Formula I.

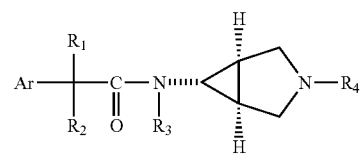

Formula III

In accordance with a fourth aspect of the present invention, there are provided compounds having the structure of Formula IV and their pharmaceutically acceptable salts, pharmaceutically acceptable solvates, ester, enantiomers, diastereomers, N-oxides, polymorphs, prodrugs, metabolites wherein $R_3$ and $R_4$ are as defined for Formula I, s represents 1 to 2, $R_9$ is H or F and $R_{10}$ is F.

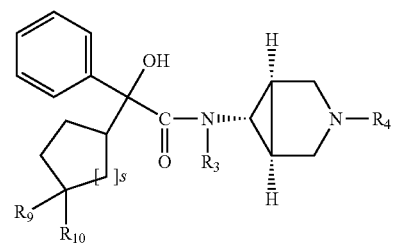

Formula IV

In accordance with a fifth aspect of the present invention, there is provided a method for treatment or prophylaxis of an animal or a human suffering from a disease or disorder of the respiratory, urinary and gastrointestinal systems, wherein the disease or disorder is mediated through muscarinic receptors, comprising administering to a patient in need thereof, an effective amount of muscarinic receptor antagonist compounds as described above.

In accordance with a sixth aspect of the present invention, there is provided a method for treatment or prophylaxis of an animal or a human suffering from a disease or disorder associated with muscarinic receptors, comprising administering to a patient in need thereof, an effective amount of muscarinic receptor antagonist compounds as described above.

In accordance with a seventh aspect of the present invention, there is provided a method for treatment or prophylaxis of an animal or a human suffering from a disease or disorder of the respiratory system such as bronchial asthma, chronic obstructive pulmonary disorders (COPD), pulmonary fibrosis, etc.; urinary system which induce such urinary disorders as urinary incontinence, as lower urinary tract symptoms (LUTS), etc.; and gastrointestinal system such as irritable bowel syndrome, obesity, diabetes and gastrointestinal hyperkinesis with compounds as described above, wherein the disease or disorder is associated with muscarinic receptors, comprising administering to a patient in need thereof, an effective amount of compounds as described above.

In accordance with an eighth aspect of the present invention, there are provided processes for preparing the compounds as described above.

The compounds of the present invention exhibit significant potency in terms of their activity, which was determined by in vitro receptor binding and functional assays. Some of the compounds of the present invention were found to be potent muscarinic receptor antagonists with high affinity towards $M_3$ receptors. Therefore, the present invention provides pharmaceutical compositions for treatment of diseases or disorders associated with muscarinic receptors. Compounds and compositions described herein can be administered orally or parenterally.

DETAILED DESCRIPTION OF THE INVENTION

The compounds described herein may be prepared by techniques well known in the art and familiar to the average synthetic organic chemist. In addition, the compounds described herein may be prepared by the following reaction sequence as shown in Scheme I.

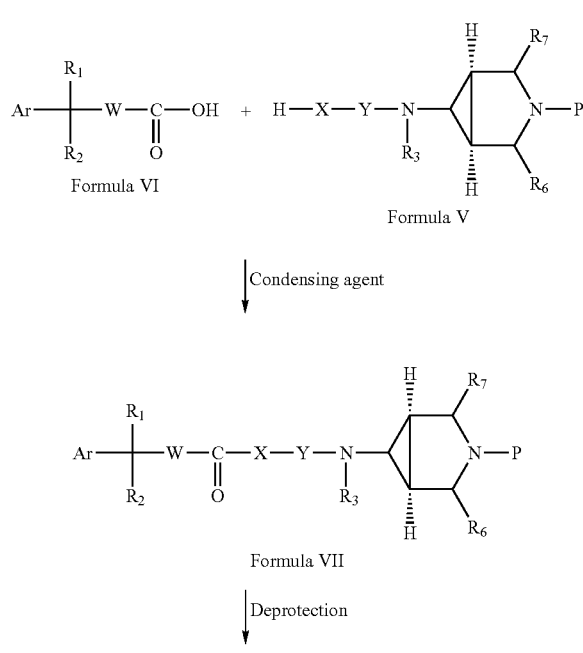

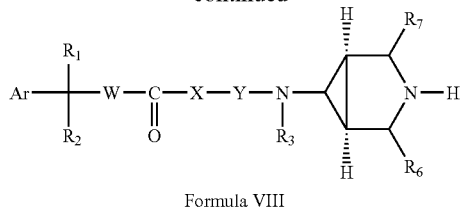

Formula VIII

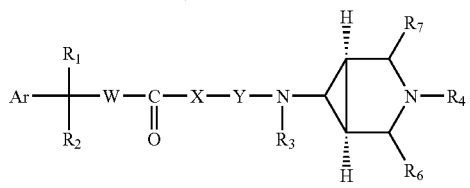

Formula I

The preparation comprises condensing a compound of Formula VI with the compound of Formula V wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhalo-alkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents alkyl, $C_3$-$C_7$ cycloalkyl ring which any 1-4 hydrogen atoms are substituted with halogen (e.g. F, Cl, Br, I), carbamoyl or lower alkyl;

W represents $(CH_2)_p$, where p represents 0 to 1;

X represents an oxygen, sulphur, NR or no atom wherein R represents hydrogen or $C_1$-$C_6$ alkyl;

Y represents $CHR_5CO$ wherein $R_5$ represents hydrogen, methyl or $(CH_2)q$ wherein q represents 0 to 4;

$R_3$ represents hydrogen, lower alkyl or $CO_2C(CH_3)_3$;

$R_6$ and $R_7$ are independently selected from H, lower alkyl, COOH, $CONH_2$, $NH_2$, or $CH_2NH_2$; and P is any group which can be used to protect an amino group, for example, benzyl, t-butyloxy carboxyl, in the presence of a condensing agent to give a protected compound of Formula VII, which on deprotection through reaction with a deprotecting agent in an organic solvent gives an unprotected compound of Formula VIII which is finally N-alkylated or benzylated with a suitable alkylating or benzylating agent L-$R_4$ to give a compound of Formula I wherein L is any leaving group and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), or N-lower alkylamino carbonyl ($C_1$-$C_4$).

The reaction of the compound of Formula VI with a compound of Formula V to give a compound of formula VII can be carried out in the presence of a condensing agent, for example, 1-(3-dimethylamino propyl)-3-ethyl carbodiimide hydrochloride (EDC) or 1,8-diazabicyclo[5.4.0]undec-7-ene (DBU).

The reaction of the compound of Formula VI with a compound of Formula V to give a compound of Formula VII can be carried out in a suitable solvent, for example, N,N-dimethylformamide, dimethylsulfoxide, toluene or xylene at a temperature ranging from about 0° C. to about 140° C.

The deprotection of the compound of Formula VII to give a compound of Formula VIII can be carried out with a deprotecting agent, for example, palladium on carbon, trifluoroacetic acid (TFA) or hydrochloric acid.

The deprotection of the compound of Formula VII to give a compound of Formula VIII can be carried out in a suitable organic solvent, for example, methanol, ethanol, tetrahydrofuran or acetonitrile at a suitable temperature ranging from about 10° C. to about 50° C.

The N-alkylation or benzylation of the compound of Formula VIII to give a compound of Formula I can be carried out with a suitable alkylating or benzylating agent, L-$R_4$ wherein L is any leaving group, known in the art, for example, halogen, O-mestyl or O-tosyl group.

The N-alkylation or benzylation of the compound of Formula VIII to give a compound of Formula I can be carried out in a suitable organic solvent such as N,N-dimethylformamide, dimethylsulfoxide, tetrahydrofuran or acetonitrile, at temperature ranging from about 25° C. to about 100° C.

Scheme II

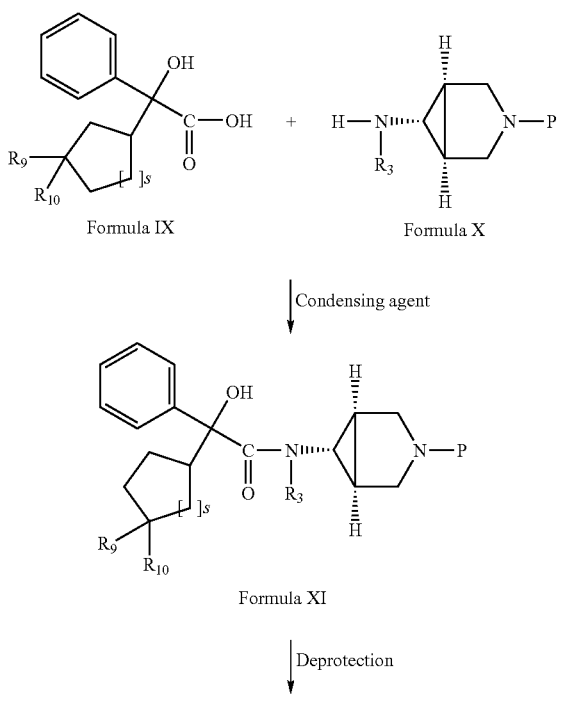

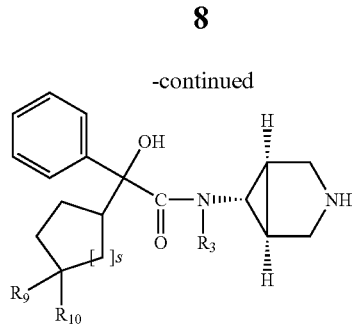

Formula XII

N-alkylation/benzylation
L$R_4$

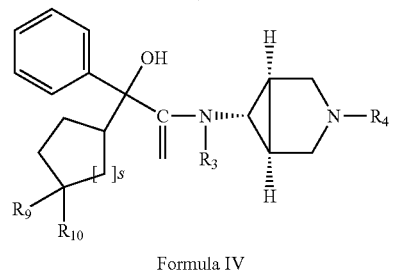

Formula IV

The compound of Formula IV of the present invention may be prepared by the reaction sequence as shown in Scheme II. The preparation comprises condensing a compound of Formula IX (prepared following the procedure described in *J. Med Chem.*, 2000; 43: 5017-5029) wherein $R_9$ is H or F and $R_{10}$ is F, with the compound of Formula X wherein $R_3$ represents hydrogen, lower alkyl, or $CO_2C(CH_3)_3$, and P is any group, for example, benzyl, t-butyloxy carbonyl which can be used to protect an amino group, in the presence of a condensing agent to give a protected compound of Formula XI, which on deprotection through reaction with a deprotecting agent in an organic solvent gives an unprotected compound of Formula XII which is finally N-alkylated or benzylated with a suitable alkylating or benzylating agent, L-$R_4$ to give a compound of Formula IV wherein L is any leaving group and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), or lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$).

The reaction of the compound of Formula IX with the compound of Formula X to give a compound of Formula XI can be carried out in the presence of a condensing agent, for example, 1-(3-dimethylaminopropyl)-3-ethyl carbodiimide hydrochloride (EDC) or 1,8-diazabicyclo [5.4.0]undec-7-ene (DBU).

The reaction of the compound of Formula IX with the compound of Formula X to give a compound of Formula XI can be carried out in a suitable solvent, for example, N,N-dimethylformamide, dimethylsulphoxide, toluene-or xylene at a temperature ranging from about 0° C. to about 25° C.

The deprotection of the compound of Formula XI to give a compound of Formula XII can be carried out in a suitable organic solvent, for example, methanol, ethanol, tetrahydrofuran or acetonitrile at a temperature ranging from about 10° C. to about 50° C.

The N-alkylation or benzylation of the compound of Formula XII to give a compound of Formula IV can be carried out with a suitable alkylating or benzylating agent, L-$R_4$ wherein L is any leaving group, known in the art, for example, halogen, O-mestyl or O-tosyl group.

The N-alkylation or benzylation of the compound of Formula XII to give a compound of Formula IV can be carried out in a suitable organic solvent such as N,N-dimethylformamide, dimethylsulphoxide, tetrahydrofuran or acetonitrile, at temperature ranging from about 0° C. to about 100° C.

The conversion of the hydroxyl or oxo group (s) to fluorine atoms(s) normally can be effected by causing the compound to react in an inert solvent which is not detrimental to the reaction, e.g., methylene chloride, chloroform, tetrahydrofuran, acetonitrile, DMSO or in pyridine or in the absence of a solvent, using one equivalent to an excessive amount of fluorinating agent belonging to a class of diethylamino sulphurtrifluoride, at temperatures ranging from about −80° C. to about 100° C.

In the above schemes, where specific bases, condensing agents, protecting groups, protecting agents, N-alkylating or benzylating agents, solvents, etc., are mentioned, it is to be understood that other basic condensing agents, protecting group, deprotecting agents, N-alkylating/benzylating agents, solvents, etc., known to those skilled in the art may be used. Similarly, the reaction temperature and duration may be adjusted according to the desired needs.

An illustrative list of particular compounds which are capable of being produced by Schemes I & II and shown in Table I include:

COMPOUND NO. CHEMICAL NAME 1. (2S)-(1α, 5α, 6α)-6-N-[3-benzyl-3-azabicyclo[3.1.0]-hexyl]-2-[(1R or 1S)-3-oxocyclohexyl]-2-hydroxy-2-phenylacetamide.
2. (2S)-(1α, 5α, 6α)-6-N-[3-benzyl-3-azabicyclo[3.1.0]-hexyl]-2[(1R or 1S, 3R or 3S)-3-(fluorocyclohexyl]-2-hydroxy-2-phenylacetamide.
3. (2S)-(1α, 5α, 6α)-6-N-[3-benzyl-3-azabicyclo[3.1.0]-hexyl]-2-[(1R or 1S, 3R or 3S)-3-fluorocyclopentyl]-2-hydroxy-2-phenylacetamide.
4. (2S)-(1α, 5α, 6α)-6-N-[3-benzyl-3-azabicyclo[3.1.0]-hexyl]-2-2[(1R or 1S)-3,3-difluorocyclohexyl]-2-hydroxy-2-phenylacetamide.
5. (2S)-(1α, 5α, 6α)-6-N-[3-benzyl-3-azabicyclo[3.1.0]-hexyl]-2-[(1R or 1S)-3,3-difluorocyclopentyl]-2-hydroxy-2-phenylacetamide.
6. (2R)-(1α, 5α, 6α)-6-N-[3-benzyl-3-azabicyclo[3.1.0]-hexyl]-2-[(1R or 1S)-3,3-difluorocyclopentyl]-2-hydroxy-2-phenylacetamide.
7. (2S)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclohexyl]-2-hydroxy-2-phenylacetamide.
8. (2S)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclopentyl]-2-hydroxy-2-phenylacetamide.
9. (2R)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclopentyl]-2-hydroxy-2-phenylacetamide.
10. (2S)-(1α, 5α, 6α)-6-N-[3-(2-(3,4-methylenedioxyphenyl)ethyl]-3-azabicyclo[3.1.0]-hexyl]-2-[(1R or 1S, 3R or 3S)-3-fluorocyclohexyl]-2-hydroxy-2-phenylacetamide.
11. (2S)-(1α, 5α, 6α)-6-N-[3-(2-(3,4-methylenedioxyphenyl)ethyl]-3-azabicyclo[3.1.0]-hexyl]-2-[(1R or 1S, 3R or 3S)-3-fluorocyclopentyl]-2-hydroxy-2-phenylacetamide.
12. (2S)-(1α, 5α, 6α)-6-N-[3-(4-methyl-3-pentenyl)-3-azabicyclo[3.1.0]-hexyl]-2-[(1R or 1S)-3,3-difluorocyclohexyl]-2-hydroxy-2-phenylacetamide.
13. (2S)-(1α, 5α, 6α)-6-N-[3-(4-methyl-3-pentenyl)-3-azabicyclo[3.1.0]-hexyl]-2-[(1R or 1S)-3,3-difluorocyclopentyl]-2-hydroxy-2-phenylacetamide.
14. (2R)-(1α, 5α, 6α)-6-N-[3-(4-methyl-3-pentenyl)-3-azabicyclo[3.1.0]-hexyl]-2-[(1R or 1S)-3,3-difluorocyclopentyl]-2-hydroxy-2-phenylacetamide.
15. (2S)-(1α, 5α, 6α)-6-N-[3-(4-methyl-3-pentenyl)-3-azabicyclo[3.1.0]-hexyl]-2-[(1R or 1S, 3R or 3S)-3-fluorocyclohexyl]-2-hydroxy-2-phenylacetamide.
16. (2S)-(1α, 5α, 6α)-6-N-[3-(4-methyl-3-pentenyl)-3-azabicyclo[3.1.0]-hexyl]-2-[(1R or 1S, 3R or 3S)-3-fluorocyclopentyl]-2-hydroxy-2-phenylacetamide.

TABLE I

Formula III

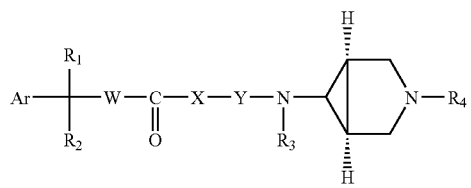

| Compound No. | Ar | $R_2$ | $R_1$ | $R_3$ | $R_4$ |
|---|---|---|---|---|---|
| 1 | phenyl | 3-oxocyclohexyl | OH | H | benzyl |

TABLE I-continued

Formula III

Ar—C(R1)(R2)—W—C(=O)—X—Y—N(R3)—[bridged bicyclic amine]—N—R4

| Compound No. | Ar | R2 | R1 | R3 | R4 |
|---|---|---|---|---|---|
| 2 | phenyl | F-cyclohexyl | OH | H | phenylethyl |
| 3 | phenyl | F-cyclopentyl | OH | H | phenylethyl |
| 4 | phenyl | F,F-cyclohexyl | OH | H | phenylethyl |
| 5 | phenyl | F,F-cyclopentyl | OH | H | phenylethyl |
| 6 | phenyl | F,F-cyclopentyl | OH | H | phenylethyl |
| 7 | phenyl | F,F-cyclohexyl | OH | H | benzo[1,3]dioxol-propyl |
| 8 | phenyl | F,F-cyclopentyl | OH | H | benzo[1,3]dioxol-propyl |
| 9 | phenyl | F,F-cyclopentyl | OH | H | benzo[1,3]dioxol-propyl |
| 10 | phenyl | F-cyclohexyl | OH | H | benzo[1,3]dioxol-propyl |
| 11 | phenyl | F-cyclopentyl | OH | H | benzo[1,3]dioxol-propyl |
| 12 | phenyl | F,F-cyclohexyl | OH | H | 4-methylpent-3-enyl |

TABLE I-continued

Formula III

| Compound No. | Ar | R₂ | R₁ | R₃ | R₄ |
|---|---|---|---|---|---|
| 13 | phenyl | 3,3-difluorocyclopentyl | OH | H | 3-methyl-2-butenyl |
| 14 | phenyl | 2,2-difluorocyclopentyl | OH | H | 3-methyl-2-butenyl |
| 15 | phenyl | 3-fluorocyclohexyl | OH | H | 3-methyl-2-butenyl |
| 16 | phenyl | 3-fluorocyclopentyl | OH | H | 3-methyl-2-butenyl |

(wherein W is $(CH_2)_p$ where p = 0, X is no atom and Y is $(CH_2)_q$ where q = 0)

Compounds or compositions disclosed may be administered to an animal for treatment orally, or by parenteral route. Pharmaceuticals compositions disclosed herein can be producted and administered in dosage units, each unit containing a certain amount of at least one compound described herein and/or at least on physiologically acceptable salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formulae I, II, III, and IV. In general, such prodrugs will be functional derivatives of these compounds, which readily are converted in vivo into the defined compounds. Conventional procedures for the selection and preparation of suitable prodrugs are known.

The present invention also includes the enantiomers, diastereomers, N-oxides, polymorphs, solvates and pharmaceutically acceptable salts of these compounds as well as metabolites having the same type of activity. The present invention further includes pharmaceutical composition comprising the molecules of Formulae I, II, III, and IV or prodrugs, metabolite enantiomers, diastereomers. N-oxides, polymorphs, solvates or pharmaceutically acceptable salts thereof, in combination with pharmaceutically acceptable carrier and optionally included excipients.

The examples mentioned below demonstrate the general synthetic procedure as well as the specific preparation of the particular compound. The examples are provided to illustrate particular aspects of the disclosure and should not be constrained to limit the scope of the present invention, as defined by the claims.

EXPERIMENTAL DETAILS

Various solvents, such as acetone, methanol, pyridine, ether, tetrahydrofuran, hexanes, and dichloromethane, were dried using various drying reagents according to the procedure described in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

EXAMPLE 1

Preparation of (2S)-(1α, 5α, 6α)-6-N-[3-benzyl-3-azabicyclo[3.1.0]-hexyl]-2-[1R or 1S)-3-oxocyclohexyl]-2-hydroxy-2-phenylacetamide (Compound No.1)

Step-a: Synthesis of (2S, 5S)-2-tert-butyl-5-phenyl-1,3-dioxalan-4-one.

The compound was synthesized following the procedure described in *J. Org. Chem.*, 2000; 65: 6283-6287, using S-(+)-Mandelic acid.

Step-b: Synthesis of (2S, 5S)-2-tert-butyl-5-[(1R or 1S)-3-oxocyclohexyl-5-phenyl-1,3-dioxolan-4-one.

Lithium diisopropylamide (6.9 mmol) was added to a solution of compound of step a (4.6 mmol) in tetrahydrofuran (40 ml) containing 2 ml of hexamethyl phosphoramide and pre-cooled to −78° C. under nitrogen atmosphere. The reaction mixture was stirred for 1 hour at the same temperature, and then cyclohexenone (9.2 mmol) diluted with 3 ml of THF was added to the reaction mixture. The mixture was further stirred for 3 hours at the same temperature. The reaction mixture was diluted with ethyl acetate, washed with saturated ammonium chloride and then with water. The organic layer was dried and the residue obtained after removing the solvent was purified by column chromatography (100-200 mesh, silica gel), eluting the compound with 10% ethyl acetate-hexane mixture.

$^1$HNMR (CDCl$_3$): 7.67-7.31 (m, 5ArH), 5.42 (d, 1H), 2.48-2.0 (m, 8H), 0.95-0.90 (d, 9H).

IR (DCM): 1714 and 1790 cm$^{-1}$

Step-c: Synthesis of (2S)-[(1R or 1S)-3-oxocyclohexyl]-2-hydroxy-2-phenylacetic acid.

The compound of step b (1 mmol) was dissolved in 5 ml methanol and aqueous sodium hydroxide (3N, 5 ml) was added. The reaction mixture was stirred at room temperature overnight. The reaction mixture was concentrated under reduced pressure, diluted with water and acidified with concentrated hydrochloric acid. It was extracted with ethyl acetate. The residue obtained after removing the solvents was purified by column chromatography (100-200 mesh, silica-gel), eluting the compound with 20% ethyl acetate-hexane mixture.

Step-d: Synthesis of (1α, 5α, 6α)-6-amino-3-benzyl-3-azabicyclo[3.1.0]hexane.

This was synthesized by following the procedure of T. F. Braish, et. al., Synlett. 1100, (1996).

Step-e: Synthesis of (2S)-(1α, 5α, 6α)-6-N-[3-benzyl-3-azabicyclo[3.1.0]-hexyl]-2-[(1R or 1S)-3-oxocyclohexyl]-2-hydroxy-2-phenylacetamide A solution of compound obtained at step c (1.21 mmol) and (1α, 5α, 6α)-6-amino-3-benzyl-3-azabicyclo[3.1.0]-hexane (1.45 mmol) was dissolved in dimethylformamide (5 ml) and cooled to 0° C. N-methylmorpholine (2.42 mmol) and 1-hydroxybenzotriazole (1.33 mmol) were added to the reaction mixture and stirred for 30 minutes at the same temperature. 1-(3-dimethylaminopropyl)-3-ethyl-carbodiimide hydrochloride (1.21 mmol) was added to the reaction mixture and the reaction mixture stirred at 0° C. for 1 hour and then at room temperature for 2 days. The reaction mixture was taken in ethyl acetate, washed with water, and dried. The residue obtained after removing the solvent was purified by column chromatography (100-200 mesh, silica gel), eluting the compound with ethyl acetate-hexane mixture.

IR (DCM): 1655 and 1706 cm$^{-1}$

EXAMPLE 2

Preparation of (2S)-(1α, 5α, 6α)-6-N-[3-benzyl-3-azabicyclo[3.1.0]-hexyl]-2-[(1R or 1S, 3R or 3S-3-fluorocyclohexyl]-2-hydroxy-2-phenylacetamide
(Compound No. 2)

Step-a: Synthesis of (2S)-tert-butyl-5-[(1R or 1S, 3R or 3S)-3-hydroxycyclohexyl]-5-phenyl-1,3-dioxalan-4-one.

The compound of Example 1, Step-b (1 mmol) was dissolved in methanol (5 ml) and cooled to 0° C. Sodium borohydride (2 mmol) was added in small lots and the reaction mixture was stirred at 0° C. for 1 hour. The solvent was removed under reduced pressure, the residue taken in ethyl acetate and washed with water. The organic layer was dried and the residue obtained after removal of solvents was used as such.

$^1$HNMR (CDCl$_3$): 7.66-7.28 (m, 5ArH), 5.40 (d, 1H), 3.6-3.4 (m, 1H), 2.04 (s, 4H), 1.21 (m, 5H), 0.92 (s, 9H)

IR (DCM): 1790 cm$^{-1}$

Step-b: Synthesis of (2S, 5S)-2-tert-butyl-5-[(1R or 1S, 3R or 3S)-3-fluorocyclohexyl)-5-phenyl-1,3-dioxalan-4-one.

To the compound of step-a (1 mmol) in dichloromethane (10 ml) at 0° C., was added diethylamino sulfur trifluoride (DAST) (1.2 mmol) and the reaction mixture was stirred at room temperature overnight. The reaction mixture was cooled to 0° C. and quenched with water. The organic layer was separated and the aqueous layer was extracted with dichloromethane. The organic layer was dried and the residue obtained after removing the solvent was purified by column chromatography (100-200 mesh, silica gel), eluting the compound with ethyl acetate-hexane mixture.

m.pt: 136-139° C.

$^1$HNMR (CDCl$_3$): 7.68-7.26 (m, 5ArH), 5.37 (t, 1H), 4.89 (m, 1H), 2.4 (m, 1H), 2.0-1.24 (m, 6H), 0.89 (d, 9H)

IR (KBr): 1787 cm$^{-1}$

Step-c: Synthesis of (2S)-[(1R or 1S, 3R or 3S)-3-fluorocyclohexyl]-2-hydroxy-2-phenyl acetic acid.

The compound was synthesized following the procedure of Example 1, step-c, using (2S)-2-tert-butyl-5-[(1R or 1S, 3R or 3S)-3-fluorocyclohexyl]-5-phenyl-1,3-dioxalan-4-one instead of (2S)-2-tert-butyl-5-[1R or 1S)]-3-oxocyclohexyl]-5-phenyl-1,3-dioxalan-4-one.

Step-d: Synthesis of (2S)-(1α, 5α, 6α)-6-N-[3-benzyl-3-azabicyclo[3.1.0]-2-[(1R or 1S, 3R or 3S)-3-fluorocyclohexyl]-2-hydroxy-2-phenylacetamide The title compound was synthesized following the procedure of Example-1, step-e, using (2S)-[(1R or 1S, 3R or 3S)-3-fluorocyclohexyl]-2-hydroxy-2-phenylacetic acid instead of (2S)-[(1R or 1S)-3-oxocyclohexyl]-2-hydroxy-2-phenylacetic acid.

$^1$HNMR (CDCl$_3$): 7.54-7.19 (m, 10ArH), 4.5 (m, 1H), 3.55 (s, 2H), 3.01 (m, 2H), 2.7 (m, 1H)

IR (KBr): 1656 cm$^{-1}$

EXAMPLE 3

Preparation of (2S)-(1α, 5α, 6α)-6-N-[3-benzyl-3-azabicyclo[3.1.0]-hexyl]-2-[(1R or 1S, 3R or 3S)-3-fluorocyclopentyl]-2-hydroxy-2-phenylacetamide
(Compound No. 3)

Step-a: Synthesis of (2S, 5S)-2-tert-butyl-5-[(1R or 1S)-3-oxocyclopentyl]-5-phenyl-1,3-dioxolan-4-one.

The compound was synthesized following the procedure of Example 1, step-b, using 2-cyclopentenone instead of 2-cyclohexenone.

$^1$HNMR (CDCl$_3$): 7.70-7.26 (m, 5ArH), 5.40 (d, 1H), 2.88 (m, 1H), 2.37-1.05 (m, 6H), 0.90 (s, 9H).

IR (DCM): 1791 and 1746 cm$^{-1}$

Step-b: Synthesis of (2S, 5S)-2-tert-butyl-5-[(1R or 1S, 3R or 3S)-3-hydroxycyclopentyl]-5-phenyl-1,3-dioxolan-4-one.

The compound was synthesized following the procedure of Example 2, step-a, using (2S, 5S)-2-tert-butyl-5-[(1R or 1S)-3-oxocyclopentyl]-5-phenyl-1,3-dioxolan-4-one instead of (2S, 5S)-2-tert-butyl-5-[(1R or 1S)-3-oxocyclohexyl]-5-phenyl-1,3-dioxolan-4-one.

¹HNMR (CDCl₃): 7.68-7.25 (m, 5ArH), 5.49 (d, 1H), 4.33-4.27 (m, 1H), 2.67-2.62 (m, 1H), 1.97-1.25 (m, 6H), 0.91 (s, 9H).
IR (DCM): 1790 cm⁻¹

Step-c: Synthesis of (2S, 5S)-2-tert-butyl-5-[(1R or 1S, 3R or 3S)-3-fluorocyclopentyl]-5-phenyl-1,3-dioxolan-4-one.

The compound was synthesized following the procedure of Example 2, step-b, using (2S, 5S)-2-tert-butyl-5-[(1R or 1S, 3R or 3S)-3-hydroxycyclopentyl]-5-phenyl-1,3-dioxolan-4-one instead of (2S, 5S)-2-tert-butyl-5-[(1R or 1S, 3R or 3S)-3-hydroxycyclohexyl]-5-phenyl-1,3-dioxolan-4-one.
IR (DCM): 1791 cm⁻¹

Step-d: Synthesis of (2S)-[(1R or 1S, 3R or 3S)-3-fluorocyclopentyl]-2-hydroxy-2-phenylacetic acid.

The compound was synthesized following the procedure of Example 1, step-c, using (2S, 5S)-2-tert-butyl-5-[(1R or 1S, 3R or 3S)-3-fluorocyclopentyl]-5-phenyl-1,3-dioxolan-4-one instead of (2S, 5S)-2-tert-butyl-5-[(1R or 1S)-3-oxocyclohexyl]-5-phenyl-1,3-dioxolan-4-one.
¹HNMR (CDCl₃): 7.67-7.25 (m, 5ArH), 5.29-4.99 (m, 1H), 3.29-3.18 (m, 1H), 2.03-1.25 (m, 6H)
IR (DCM): 1726 cm⁻¹

Step-e: Synthesis of (2S)-(1α, 5α, 6α)-6-N-[3-benzyl-3-azabicyclo[3.1.0]-hexyl]-2-(1R or 1S, 3R or 3S)-3-fluorocyclopentyl]-2-hydroxy-2-phenylacetamide The title compound was synthesized following the procedure of Example 1, step-e, using (2S)-[(1R or 1S, 3R or 3S)-3-fluorocyclopentyl]-2-hydroxy-2-phenylacetic acid instead of (2S)-[(1R or 1S)-3-oxocyclohexyl]-2-hydroxy-2-phenylacetic acid.
¹HNMR (CDCl₃): 7.67-7.19 (m, 10ArH), 5.2 (m, 1H), 3.52 (s, 2H), 3.08-2.97 (m, 6H), 2.33-1.25 (m, 8H).
IR (DCM): 1653 cm⁻¹

EXAMPLE 4

Preparation of (2S)-(1α, 5α, 6α)-6-N-[3-benzyl-3-azabicyclo[3.1.0]-hexyl]-2-[(1R or 1S)-3,3-difluorocyclohexyl]-2-hydroxy-2-phenylacetamide (Compound No. 4A & 4B)

Step-a: Synthesis of (2S, 5S)-2-tert-butyl-5-[1R or 1S)-3,3-difluorocyclohexyl]-5-phenyl-1,3-dioxolan-4-one.

To a solution of (2S, 5S)-2-tert-butyl-5-[(1R or 1S)-3-oxocyclohexyl]-5-phenyl-1,3-dioxolan-4-one (1 mmol) in chloroform cooled to 0° C., was added diethylamino sulfur trifluoride (DAST) (4 mmol). The reaction mixture was stirred at room temperature overnight. The reaction mixture was cooled and quenched with water. The organic layer was separated and the aqueous layer was extracted with dichloromethane. The organic layer was dried and the residue obtained after removal of solvents was purified by column chromatography (100-200 mesh, silica gel), eluting the compound with 5% ethyl acetate-hexane mixture.
¹HNMR (CDCl₃): 7.67-6.29 (m, 5ArH), 5.39 (d, 1H), 2.32 (m, 1H), 2.1-1.25 (m, 8H), 0.93 (8, 9H)
IR (DCM): 1792 cm⁻¹

Step-b: Synthesis of (2S)-[(1R or 1S)-3,3-difluorocyclohexyl]-2-hydroxy-2-phenylacetic acid.

The compound was synthesized following the procedure of Example 1, step-c, using (2S)-2-tert-butyl-5-[(1R or 1S)-3,3-difluorocyclohexyl]-5-phenyl-1,3-dioxolan-4-one instead of (2S)-2-tert-butyl-5-[(1R or 1S)-3-oxocyclohexyl]-5-phenyl-1,3-dioxolan-4-one.
m.pt: 144-147° C.
IR (KBr): 1694 cm⁻¹

Step-c: Synthesis of (2S)-(1α, 5α, 6α)-6-N-[3-benzyl-3-azabicyclo[3.1.0]-hexyl]-2-[(1R or 1S)-3,3-difluorocyclohexyl]-2-hydroxy-2-phenylacetamide The above compound was synthesized following the procedure of Example 1, step-e, using (2S)-2-[(1R or 1S)-3,3-difluorocyclohexyl]-2-phenylacetic acid instead of (2S)-2-[(1R or 1S)-3-oxocyclohexyl]-2-hydroxy-2-phenylacetic acid.

Compound 4A: ¹HNMR (CDCl₃): 7.57-7.13 (m, 10ArH), 3.53 (s, 2H), 2.99 (m, 3H).
IR (DCM): 1653 cm⁻¹

Compound 4B: ¹HNMR (CDCl₃): 7.59-7.19 (m, 10ArH), 3.53 (s, 2H), 3.06 (m, 3H).
IR (DCM): 1652 cm⁻¹

Compounds 4A & 4B are a pair of diastereomers.

EXAMPLE 5

Preparation of (2S)-(1α, 5α, 6α)-6-N-[3-benzyl-3-azabicyclo [3.1.0]-hexyl]-2[(1R or 1S)-3,3-difluorocyclopentyl]-2-hydroxy-2-phenylacetamide (Compound No. 5A & 5B)

Step-a: Synthesis of (2S, 5S)-2-tert-butyl-5-[(1R or 1S)-3,3-difluorocyclopentyl]-5-phenyl-1,3-dioxolan-4-one.

The compound was synthesized following the procedure of Example 4, step-a, using (2S, 5S)-2-tert-butyl-5-[(1R or 1S)-3-oxocyclopentyl]-5-phenyl-1,3-dioxolan-4-one instead of (2S, 5S)-2-tert-butyl-5-[(1R or 1S)-3-oxocyclohexyl]-5-phenyl-1,3-dioxolan-4-one.
¹HNMR (CDCl₃): 7.67-7.25 (m, 5H), 5.42 (s, 1H), 2.80-2.76 (m, 1H), 2.21-1.74 (m, 6H),) 0.95 (s, 9H)
IR (DCM): 1793 cm⁻¹

Step-b: Synthesis of (2S)-[(1R or 1S)-3,3-difluorocyclopentyl]-2-hydroxy-2-phenylacetic acid.

The compound was synthesized following the procedure of Example 1, step-c using (2S)-2-tert-butyl-5-[(1R or 1S)-3,3-difluorocyclopentyl]-5-phenyl-1,3-dioxolan-4-one instead of (2S)-2-tert-butyl-5-[(1R or 1S)-3-oxocyclohexyl]-5-phenyl-1,3-dioxolan-4-one.
m.pt: 127° C.
¹HNMR (CDCl₃): 7.63-7.25 (m, 5H), 3.22-3.10 (m, 1H), 2.26-1.25 (m, 6H).
IR (DCM): 1712 cm⁻¹

Step-c: Synthesis of (2S)-(1α, 5α, 6α)-6-N-[3-benzyl-3-azabicyclo[3.1.0]-hexyl]-2-[(1R or 1S)-3,3-difluorocyclopentyl)]-2-hydroxy-2-phenylacetamide.

The title compound was synthesized following the procedure of Example 1, step-e, using (2S)-[(1R or 1S)-3,3-difluorocyclopentyl]-2-hydroxy-2-phenylacetic acid instead of (2S)-[(1R or 1S)-3-oxocyclohexyl]-2-hydroxy-2-phenylacetic acid.

Compound 5A
¹HNMR (CDCl₃): 7.55-7.19 (m, 10ArH), 6.23 (brs, 1H), 3.52 (s, 2H), 3.38 (s, 1H), 3.30-3.22 (m, 1H), 3.06-2.98 (m, 3H), 2.36-2.32 (m, 2H), 2.14-2.04 (m, 4H), 1.56-1.25 (m, 4H)
IR (DCM): 1656 cm⁻¹

Compound 5B
¹NMR (CDCl₃): 7.54-7.19 (m, 10ArH), 6.30 (brs, 1H), 3.52 (s, 2H), 3.37-3.24 (m, 2H), 3.06-2.98 (m, 3H), 2.36-1.25 (m, 10H).

IR (DCM): 1652 cm$^{-1}$
Compounds 5A and 5B are a pair of diastereomers.

EXAMPLE 6

Preparation of (2R)-(1α, 5α, 6α)-6-N-[3-benzyl-3-azabicyclo [3.1.0]-hexyl]-2-[(1R or 1S)-3,3-difluoro-cyclopentyl]-2-hydroxy-2-phenylacetamide (Compound No. 6)

Step-a: Synthesis of (2R, 5R)-2-tert-butyl-5-phenyl-1,3-dioxalan-4-one.
This compound was synthesized following the procedure described in J. Org. Chem. 2000; 65: 6283-6287.

Step-b: Synthesis of (2R, 5R)-2-tert-butyl-5-[(1R or 1S)-3-oxocyclopentyl]-5-phenyl-1,3-dioxolan-4-one.
The compound was synthesized following the procedure of Example 1, step-b, using (2R, 5R)-2-tert-butyl-5-phenyl-1,3-dioxalan-4-one instead of (2S, 5S)-2-tert-butyl-5-phenyl-1,3-dioxalan-4-one and 2-cyclopentenone instead of 2-cyclohexenone.

Step-c: Synthesis of (2R, 5R)-2-tert-butyl-5-[(1R or 1S)-3,3-difluorocyclopentyl]-5-phenyl-1,3-dioxolan-4-one.
The compound was synthesized following the procedure of Example 4, step-a, using (2R, 5R)-2-tert-butyl-5-[(1R or 1S)-3-oxocyclopentyl]-5-phenyl-1,3-dioxolan-4-one instead of (2S, 5S)-2-tert-butyl-5-[(1R or 1S)-3-oxocyclopentyl]-5-phenyl-1,3-dioxolan-4-one.
$^1$HNMR (CDCl$_3$): 7.67-7.25 (m, 5ArH), 5.43 (s, 1H), 2.79-2.76 (m, 1H), 2.23-1.67 (m, 6H), 0.92 (s, 9H)
IR (DCM): 1792 cm$^{-1}$ Step-d: Synthesis of (2R)-[(1R or 1S)-3,3-difluorocyclopentyl]-2-hydroxy-2-phenylacetic acid.
The compound was synthesized following the procedure of Example-1, Step-c, using (2R, 5R)-2-tert-butyl-5-[(1R or 1S)-3,3-difluorocyclopentyl]-5-phenyl-1,3-dioxolan-4-one instead of (2S, 5S)-2-tert-butyl-5-[(1R or 1S)-3-oxocyclohexyl]-5-phenyl-1,3-dioxolan-4-one.
$^1$HNMR (CDCl$_3$): 7.64-7.25 (m, 5ArH), 3.22-3.10 (m, 1H), 2.26-1.43 (m, 6H)
IR (KBr): 1724 cm$^{-1}$ Step-e: Synthesis of (2R)-(1α, 5α, 6α)-6N-[3-benzyl-3-azabicyclo[3.1.0]-hexyl]-2-[1R or 1S)-3,3-difluorocyclopentyl]-2-hydroxy-2-phenylacetamide.
The title compound was synthesized following the procedure of Example 1, step-e, using (2R)-[(1R or 1S)-3,3-difluorocyclopentyl]-2-hydroxy-2-phenylacetic acid instead of (2S)-[(1R or 1S)-3-oxocyclohexyl]-2-hydroxy-2-phenylacetic acid.
$^1$HNMR (CDCl$_3$): 7.54-7.19 (m, 10ArH), 5.77 (brs, 1H), 3.52 (s, 2H), 3.30-2.98 (m, 6H), 2.35-2.31 (m, 2H), 2.13-1.10 (m, 7H).
IR (DCM): 1651 cm$^{-1}$

EXAMPLE 7

Preparation of (2S)-(1α, 5α, 6α)-6-N-[3-2-(-(3,4-methylenedioxyphenyl)ethyl]-3-azabicyclo[3.1.0]-hexyl-2-[(1R or 1S)-3,3-difluorocyclohexyl]-2-hydroxy-2-phenylacetamide (Compound No. 7)

Step-a: Synthesis of 3,4-methylenedioxyphenethyl bromide.
The compound was synthesized following the procedure described in EP 0388054A1.

Step-b: Synthesis of (1α,5α,6α)-6-tert-butoxycarbonylamino-3-azabicyclo[3.1.0]hexane
The compound was synthesized following the procedure described in T. F. Braish et.al., Synlett., 1100, (1996).

Step-c: Synthesis of (1α, 5α, 6α)-3N-[2-(3,4-methylenedioxyphenyl)ethyl]-6-[t-butoxycarbonyl amino]-3-azabicyclo-[3.1.0]hexane
A solution of compound obtained in step b (1.5 mmol) and methylenedioxyphenethyl bromide (1 mmol) in acetonitrile (10 ml) containing potassium carbonate (3 mmol) and potassium iodide (1.5 mmol) was refluxed for 6 hours. The solvent was removed under reduced pressure, the residue was taken in ethyl acetate, and washed with water. The organic layer was then dried and the residue obtained after removal of solvent was purified by column chromatography (100-200 mesh, silica gel), using ethyl acetate-hexane mixture as eluent.
$^1$HNMR (CDCl$_3$): 6.72-6.59 (m, 3ArH), 5.9 (s, 2H), 3.12 (d, 2H), 2.75 (s, 1H), 2.54 (m, 4H), 2.36 (d, 2H), 1.43 (d, 1H).

Step-d: Synthesis of (1α, 5α, 6α)-3-N-[2-(3,4-methylenedioxyphenyl)ethyl]-3-azabicyclo[3.1.0]hexane hydrochloride.
The compound of step-c was dissolved in ethyl acetate and ethyl acetate saturated with hydrochloric acid was added to the above reaction mixture and stirred overnight at room temperature. The solvent was removed under reduced pressure and the residue was washed with hexane and dried.
m. pt: 232° C.

Step-e: Synthesis of (2S)-(1α,5α,6α)-6-N-[3-(2-(3,4-methylenedioxyphenyl)ethyl]-3-azabicyclo[3.1.0]-hexyl-2-[(1R or 1S)-3,3-difluorocyclohexyl]-2-hydroxy-2-phenylacetamide
A solution of (2S)-[(1R or 1S)-3,3-difluorocyclohexyl]-2-hydroxy-2-phenylacetic acid (1 mmol) and the amine of step-d (1 mmol) in dimethylformamide (5 ml) was cooled to 0° C. Hydroxybenzotriazole (HOBT) (1 mmol) and N-methylmorpholine (4 mmol) were added to the reaction mixture and the reaction mixture was stirred at 0° C. for 30 minutes. 1-(3-dimethyl amino propyl)-3-ethyl-carbodiimide hydrochloride was added to the reaction mixture and stirred at 0° C. for 1 hour and then at room temperature for 1 day. The reaction mixture was poured into saturated bicarbonate solution and extracted with ethyl acetate. The organic layer was washed with water, dried and the residue obtained after removal of solvent was purified by column chromatography (100-200 mesh, silica gel), eluting the compound with 50% ethyl acetate-hexane mixture.
$^1$HNMR (CDCl$_3$): 7.53-7.3 (m, 5ArH), 6.7-6.58 (m, 3ArH), 5.9 (s, 2H), 3.15 (t, 2H).
IR (KBr): 1662 cm$^{-1}$

EXAMPLE 8

Preparation of (2S)-(1α, 5α, 6α)-6N-[3-(2-(3,4-methylenedioxyphenyl)ethyl)]-3-azabicyclo[3.1.0]-hexyl-2-[(1R or 1S)-3,3-difluorocyclopentyl]-2-hydroxy-2-phenylacetamide (Compound No. 8A & 8B)

The title compound was synthesized following the procedure of Example 7, step-e, using (2S)-[(1R or 1S)-3,3-difluorocyclopentyl]-2-hydroxy-2-phenyl acetic acid instead of (2S)-[(1R or 1S)-3,3-difluorocyclohexyl]-2-hydroxy-2-phenyl acetic acid.

Compound 8A

¹HNMR (CDCl₃): 7.57-7.26 (m, 5ArH), 6.71-6.58 (m, 3H), 6.30 (brs, 1H), 5.90 (s, 2H), 3.27-2.02 (m, 10H), 1.76-1.23 (m, 8H).

Compound 8B

¹HNMR (CDCl₃): 7.54-7.26 (m, 5ArH), 6.70-6.57 (m, 3ArH), 6.32 (brs, 1H), 5.89 (s, 2H), 3.27-2.31 (m, 9H), 1.85-1.25 (m, 10H)

IR (DCM): 1653 cm⁻¹

Compounds 8A and 8B are a pair of diastereomers.

EXAMPLE 9

Preparation of (2R)-(1α, 5α, 6α)-6-N-[3-(2-(3,4-methylenedioxyphenyl)ethyl-]-3-azabicyclo[3.1.0]-hexyl-2-[(1R or 1S)-3,3-difluorocyclopentyl]-2-hydroxy-2-phenylacetamide (Compound No. 9)

The title compound was synthesized following the procedure of Example 7, Step-e, using (2R)-[(1R or 1S)-3,3-difluorocyclopentyl]-2-hydroxy-2-phenyl acetic acid instead of (2S)-[(1R or 1S)-3,3-difluorocyclohexyl]-2-hydroxy-2-phenylacetic acid.

¹HNMR (CDCl₃): 7.55-7.26 (m, 5ArH), 6.70-6.57 (m, 3H), 6.30 (brs, 1H), 5.9 (s, 2H), 3.42-2.84 (m, 5H), 2.58-1.39 (m, 13H)

IR (DCM): 1651 cm⁻¹

EXAMPLE 10

Preparation of (2S)-(1α, 5α, 6α)-6-N-[3-(2-(3,4-methylenedioxyphenyl)ethyl]-3-azabicyclo[3.1.0]-hexyl-2-[1R or 1S, 3R or 3S)-3-fluorocyclohexyl]-2-hydroxy-2-phenylacetamide (Compound No. 10)

The title compound was synthesized following the procedure of Example 7, Step-e, using (2S)-(1R or 1S, 3R or 3S)-3-fluorocyclohexyl]-2-hydroxy-2-phenylacetamide instead of (2S)-[(1R or 1S)-3,3-difluorocyclohexyl]-2-hydroxy-2-phenylacetic acid.

¹HNMR (CDCl₃): 7.54-7.28 (m, 5ArH), 6.7-6.57 (m, 3ArH), 5.89 (s, 2H), 4.5 (m, 1H), 3.13 (t, 2H)

IR (KBr): 1661 cm⁻¹

EXAMPLE 11

Preparation of (2S)-(1α, 5α, 6α-6-N-[3-(2-(3,4-methylenedioxyphenyl)ethyl)]-3-azabicyclo[3.1.0]-hexyl-2-[(1R or 1S, 3R or 3S)-3-fluorocyclopentyl]-2-hydroxy-2-phenylacetamide (Compound No. 11)

The title compound was synthesized following the procedure of Example 7, Step-e, using (2S)-[1R or 1S, 3R or 3S)-3-fluorocyclopentyl]-2-hydroxy-2-phenylacetamide instead of (2S)-[(1R or 1S)-3,3-difluorocyclohexyl]-2-hydroxy-2-phenylacetic acid.

¹HNMR (CDCl₃): 7.54-7.25 (m, 5ArH), 6.70-6.57 (m, 3ArH), 5.92 (s, 2H), 5.29-5.01 (m, 1H), 3.16-2.31 (m, 9H), 2.04-1.25 (m, 10H)

IR (KBr): 1650 cm⁻¹

EXAMPLE 12

Preparation of (2S)-(1α, 5α, 6α)-6N-[3-(4-methyl-3-pentenyl)-(3-azabicyclo[3.1.0]-hexyl-2-[(1R or 1S)-3,3-difluorocyclohexyl]-2-hydroxy-2-phenylacetamide (Compound No. 12A & 12B)

Step-a: Synthesis of (1α, 5α, 6α)-3-N-(4-methyl-3-pentenyl]-6-t-butoxycarbonyl amino]-3-azabicyclo[3.1.0]hexane.

The compound was synthesized following he procedure of Example 7, Step-c, using 5-bromo-2-methyl pent-3-ene instead of 3,4-dimethylenedioxyphenethyl bromide.

¹HNMR (CDCl₃): 5.07 (t, 1H), 4.56 (bs, 1H), 3.10 (d, 1H), 2.76 (s, 1H), 2.36-2.03 (m, 6H), 1.67-1.25 (m, 18H)

IR (KBr): 1706 cm⁻¹

Step-b: Synthesis of (1α,5α,6α)-3-N-(4-methyl-3-pentenyl]-3-azabicyclo[3.1.0]hexane hydrochloride The compound was synthesized following the procedure of Example 7, step-d, using (1α, 5α, 6α)-3-N-(4-methyl-3-pentenyl]-6-t-butoxycarbonyl amino]-3-azabicyclo[3.1.0]hexane instead of (1α,5α,6α)-3-N-[2-(3,4-methylenedioxyphenyl)ethyl]-6-t-butoxycarbonyl amino]-3-azabicyclo[3.1.0] hexane.

m.pt.: 230° C.

Step-c: Synthesis of (2S)-(1α,5α,6α)-6-N-[3-(4-methyl-3-pentenyl)-3-azabicyclo[3.1.0]-hexyl-2-[(1R or 1S)-3,3-difluorocyclohexyl]-2-hydroxy-2-phenylacetamide A solution of (2S)-[(1R or 1S)-3,3-difluorocyclohexyl]-2-hydroxy-2-phenyl acetic acid (1 mmol) and compound of step-b, in DWF (5 ml) was cooled to 0° C. Hydroxy benzotriazole HOBT (1 mmol) and N-methylmorpholine NMM (4 mmol) were added to reaction mixture and stirred for 30 minutes at 0° C. 1-(3-dimethylaminopropyl)-3-ethyl carbodiimide hydrochloride (EDC. HCl) was then added to the reaction mixture and stirred for 1 hour at 0° C. followed by stirring at room temperature overnight. The reaction mixture was poured into saturated bicarbonate solution and extracted with ethyl acetate. The organic layer was washed with water, dried and the residue obtained after removal of solvents was purified by column chromatography (100-200 mesh, silica gel), eluting the compound with 30% ethyl acetate-hexane mixture.

Compound No. 12A

¹HNMR (CDCl₃): 7.59-7.29 (m, 5ArH), 5.04 (t, 1H), 3.13 (t, 2H)

IR (DCM): 1653 cm⁻¹

Compound No. 12B

¹HNMR (CDCl₃): 8.0-7.29 (m, 5ArH), 5.04 (t, 1H), 3.1 (t, 2H)

IR(DCM): 1667 cm⁻¹

Compounds 12A and 12B are a pair of diastereomers.

EXAMPLE 13

Preparation of (2S)-(1α, 5α, 6α)-6-N-[3-(4-methyl-3-pentenyl)-3-azabicyclo[3.1.0]-hexyl-2-[(1R or 1S)-3,3-difluorocyclopentyl]-2-hydroxy-2-phenylacetamide (Compound No. 13A & 13B)

The compound was synthesized following the procedure of Example 12, step-c, using (2S)-[(1R or 1S)-3,3-difluorocyclopentyl)-2-hydroxy-2-phenyl acetic acid instead of (2S)-[(1R or 1S)-3,3-difluorocyclohexyl)-2-hydroxy-2-phenylacetic acid.

Compound 13A $^1$HNMR (CDCl$_3$): 7.60-7.26 (m, 5ArH), 6.30 (brs, 1H), 5.04 (t, 1H), 3.48-2.86 (m, 4H), 2.36-1.40 (m, 21H)

Compound 13B $^1$NMR (CDCl$_3$): 7.54-7.26 (m, 5ArH), 6.44 (brs, 1H), 5.03 (t, 1H), 3.30-2.85 (m, 4H), 2.41-0.93 (m, 21H)

IR (DCM): 1655 cm$^{-1}$

Compounds 13A and 13B are a pair of diastereomers.

EXAMPLE 14

Preparation of (2S)-(1α, 5α, 6α)-6-N-[3-(4-methyl-3-pentenyl)3-azabicyclo[3.1.0]-hexyl-2-[(1R or 1S)-3,3-difluorocyclopentyl]-2-hydroxy-2-phenylacetamide (Compound No. 14)

The compound was synthesized following the procedure of Example 12, step-c, using (2R)-[(1R or 1S)-3,3-difluorocyclopentyl]-2-hydroxy-2-phenylacetic acid instead of (2S)-[(1R or 1S)-3,3-difluorocyclohexyl]-2-hydroxy-2-phenyl acetic aicd.

$^1$HNMR (CDCl$_3$): 7.58-7.26 (m, 5ArH), 6.30 (brs, 1H), 5.04 (t, 1H), 3.26.2.86 (m, 4H), 2.35-1.25 (m, 20H)

IR (DCM): 1652 cm$^{-1}$

EXAMPLE 15

Preparation of (2S)-(1α, 5α, 6α)-6-N-[3-(4-methyl-3-pentenyl)-3-azabicyclo[3.1.0]-hexyl-2-[(1R or 1S, 3R or 3S)-3-fluorocyclohexyl]-2-hydroxy-2-phenylacetamide (Compound No. 15)

The compound was synthesized following the procedure of Example 12, step-c, using (2S)-[(1R or 1S, 3R or 3S)-3-fluorocyclohexyl]-2-hydroxy-2-phenylacetic acid instead of (2S)-[1R or 1S)-3,3-difluorocyclohexyl]-2-hydroxy-2-phenylacetic acid.

$^1$HNMR (CDCl$_3$): 7.6-7.26 (m, 5ArH), 5.01 (m, 2H), 3.11 (s, 2H).

IR (DCM): 1654 cm$^{-1}$

EXAMPLE 16

Preparation of (2S)-(1α, 5α, 6α)-6-N-[3-(4-methyl-3-pentenyl)-3-azabicyclo[3.1.0]-hexyl-2-[(1R or 1S, 3R or 3S)-3-fluorocyclopentyl]-2-hydroxy-2-phenylacetamide (Compound No. 16)

The compound was synthesized following the procedure of Example 12, step-c, using (2S)-[(1R or 1S, 3R or 3S)-3-fluorocyclopentyl]-2-hydroxy-2-phenylacetic acid instead of (2S)-[(1R or 1S)-3,3-difluorocyclohexyl]-2-hydroxy-2-phenylacetic acid.

$^1$HNMR (CDCl$_3$): 7.65-7.26 (m, 5ArH), 5.20 (m, 1H), 5.04 (t, 1H), 3.13-2.85 (m, 5H), 2.35-1.25 (m, 19H)

IR (DCM): 1653 cm$^{-1}$

Biological Activity

Radioligand Binding Assays:

The affinity of test compounds for M$_2$ and M$_3$ muscarinic receptor subtypes was determined by [$^3$H]-N-methylscopolamine binding studies using rat heart and submandibular gland respectively as described by Moriya et al., (Life Sci, 1999,64(25): 2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150-250 µg protein) were incubated in 250 µl of assay buffer (HEPES 20 mM, pH 7.4) at 24-25° C. for 3 h. Non-specific binding was determined in the presence of 1 µM atropine. The incubation was terminated by vaccum filtration over GF/B fiber filters (Wallac). The filters were then washed with ice cold 50 mM Tris HCl buffer (pH 7.4). The filter mats were dried and bound radioactivity retained on filters was counted. The IC$_{50}$ & Kd were estimated by using the non-linear curve-fitting program using G Pad Prism software. The value of inhibition constant Ki was calculated from competitive binding studies by using Cheng & Prusoff equation (Biochem Pharmacol, 1973,22: 3099-3108), Ki=IC$_{50}$/(1+L/Kd), where L is the concentration of [$^3$H]NMS used in the particular experiment.

Functional Experiments using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; CaCl$_2$ 1.8; MgCl$_2$ 0.1; NaHCO$_3$ 11.9; NaH$_2$PO$_4$ 0.4; Glucose 5.55 and continuously gassed with 95% O$_2$ and 5% CO$_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period, the stabilization of the tissue contractile response was assessed with 1 µMol/L of Carbachol consecutively for 2-3 times. Subsequently, a cumulative concentration response curve to carbachol (10$^{-9}$ mol/L to 3×10$^{-5}$ mol/L) was obtained. After several washes, once the baseline was achieved, cumulative concentration response curve was obtained in the presence of NCE (NCE added 20 min. prior to the second CRC).

The contractile results were expressed as % of control E max. ED50 values were calculated by fitting a non-linear regression curve (Graph Pad Prism). pKB values were calculated by the formula pK$_B$=−log[(molar concentration of antagonist/(dose ratio−1))] where, dose ratio=ED50 in presence of antagonist/ED50 in the absence of antagonist.

The results of the in-vitro tests are listed in Table II.

In Vitro Tests

TABLE II

| Compound No. | Receptor Binding Assay | | Functional Assay |
|---|---|---|---|
| | M$_2$ (pki) | M$_3$ (pki) | pk$_B$ |
| 6 | 5.35 | 6.86 | — |
| 9 | 5.37 | 7.1 | — |
| 11 | 5.2 | 7.2 | — |
| 12B | 4.8 | 6.2 | 6.83 |
| 13B | <5 | 5.7 | 7.17 |

TABLE II-continued

| | Receptor Binding Assay | | Functional Assay |
| --- | --- | --- | --- |
| Compound No. | $M_2$ (pki) | $M_3$ (pki) | $pk_B$ |
| 14 | <5 | 5.8 | 6.88 |
| 16 | 4.9 | 6 | 7.17 |

While the present invention has been described in terms of its specific embodiments, certain modifications and equivalents will be apparent to those skilled in the art and are intended to be included within the scope of the present invention.

We claim:
1. Compounds having the structure of Formula I:

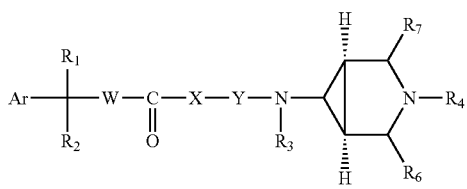

Formula I and their pharmaceutically acceptable salts, pharmaceutically acceptable enantiomers, diastereomers, or N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhalo-alkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents alkyl, $C_3$-$C_7$ cycloalkyl ring in which any 1-4 hydrogen atoms are substituted with halogen (e.g. F, Cl, Br, I), carbamoyl or lower alkyl;

W represents $(CH_2)_p$, where p represents 0 to 1;

X represents an oxygen, sulphur, NR or no atom wherein R represents hydrogen or $C_1$-$C_6$ alkyl;

Y represents $CHR_5CO$ wherein $R_5$ represents hydrogen, methyl or $(CH_2)q$ wherein q represents 0 to 4;

$R_3$ represents hydrogen, lower alkyl or $CO_2C(CH_3)_3$;

$R_6$ and $R_7$ are independently selected from H, lower alkyl, COOH, $CONH_2$, $NH_2$, $CH_2NH_2$; and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), or N-lower alkylamino carbonyl ($C_1$-$C_4$).

2. A compound according to claim 1 having the structure of Formula II and its pharmaceutically acceptable salts, pharmaceutically acceptable enantiomers, diastereomers, N-oxides, wherein
Ar, $R_1$, $R_2$, W, X, Y, $R_3$ and $R_4$ are as defined for formula I,

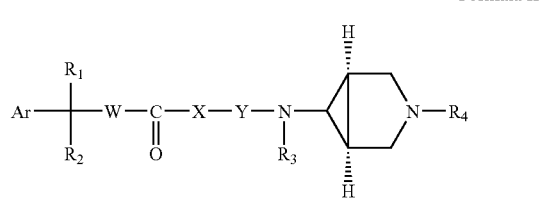

Formula II

3. A compound according to claim 1 having the structure of Formula III and its pharmaceutically acceptable salts, pharmaceutically acceptable enantiomers, diastereomers, N-oxides, wherein Ar, $R_1$, $R_2$, $R_3$ and $R_4$ are as defined for Formula I,

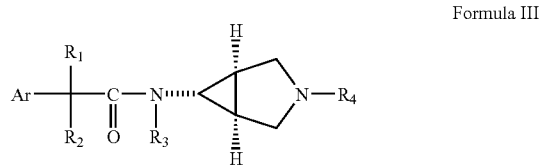

Formula III

4. A compound according to claim 1 having the structure of Formula IV and its pharmaceutically acceptable salts, enantiomers, diastereomers, N-oxides, wherein $R_3$ and $R_4$ are as defined for Formula I, and s represents 1 to 2, $R_9$ is H or F and $R_{10}$ is F,

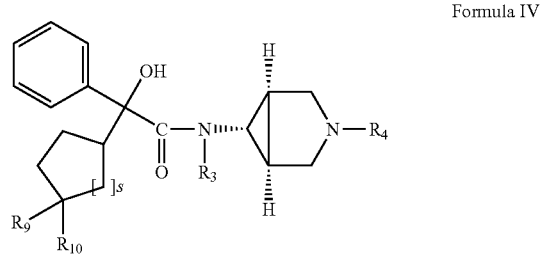

Formula IV

5. A compound selected from the group consisting of
(2S)-(1α, 5α, 6α)-6-N-[3-benzyl-3-azabicyclo[3.1.0]-hexyl]-2-[(1R or 1S)-3-oxocyclohexyl]-2-hydroxy-2-phenylacetamide;

(2S)-(1α, 5α, 6α)-6-N-[3-benzyl-3-azabicyclo[3.1.0]-hexyl]-2[(1R or 1S, 3R or 3S)-3-(fluorocyclohexyl]-2-hydroxy-2-phenylacetamide;

(2S)-(1α, 5α, 6α)-6-N-[3-benzyl-3-azabicyclo[3.1.0]-hexyl]-2-[(1R or 1S, 3R or 3S)-3-fluorocyclopentyl]-2-hydroxy-2-phenylacetamide;

(2S)-(1α, 5α, 6α)-6-N-[3-benzyl-3-azabicyclo[3.1.0]-hexyl]-2-2[(1R or 1S)-3,3-difluorocyclohexyl]-2-hydroxy-2-phenylacetamide;

(2S)-(1α, 5α, 6α)-6-N-[3-benzyl-3-azabicyclo[3.1.0]-hexyl]-2-[(1R or 1S)-3,3-difluorocyclopentyl]-2-hydroxy-2-phenylacetamide;

(2R)-(1α, 5α, 6α)-6-N-[3-benzyl-3-azabicyclo[3.1.0]-hexyl]-2-[(1R or 1S)-3,3-difluorocyclopentyl]-2-hydroxy-2-phenylacetamide;

(2S)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclohexyl]-2-hydroxy-2-phenylacetamide;

(2S)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclopentyl]-2-hydroxy-2-phenylacetamide;

(2R)-(1α, 5α, 6α)-6-N-[3-(2-(3,4-methylenedioxyphenyl)ethyl]-3-azabicyclo[3.1.0]-hexyl]-2-[(1R or 1S)-3,3-difluorocyclopentyl]-2-hydroxy-2-phenylacetamide;

(2S)-(1α, 5α, 6α)-6-N-[3-(2-(3,4-methylenedioxyphenyl)ethyl]-3-azabicyclo[3.1.0]-hexyl]-2-[(1R or 1S, 3R or 3S)-3-fluorocyclohexyl]-2-hydroxy-2-phenylacetamide;

(2S)-(1α, 5α, 6α)-6-N-[3-(2-(3,4-methylenedioxyphenyl)ethyl]-3-azabicyclo[3.1.0]-hexyl]-2-[(1R or 1S, 3R or 3S)-3-fluorocyclopentyl]-2-hydroxy-2-phenylacetamide;

(2S)-(1α, 5α, 6α)-6-N-[3-(4-methyl-3-pentenyl)-3-azabicyclo[3.1.0]-hexyl]-2-[(1R or 1S)-3,3-difluorocyclohexyl]-2-hydroxy-2-phenylacetamide;

(2S)-(1α, 5α, 6α)-6-N-[3-(4-methyl-3-pentenyl)-3-azabicyclo[3.1.0]-hexyl]-2-[(1R or 1S)-3,3-difluorocyclopentyl]-2-hydroxy-2-phenylacetamide;

(2R)-(1α, 5α, 6α)-6-N-[3-(4-methyl-3-pentenyl)-3-azabicyclo[3.1.0]-hexyl]-2-[(1R or 1S)-3,3-difluorocyclopentyl]-2-hydroxy-2-phenylacetamide;

(2S)-(1α, 5α, 6α)-6-N-[3-(4-methyl-3-pentenyl)-3-azabicyclo[3.1.0]-hexyl]-2-[(1R or 1S, 3R or 3S)-3-fluorocyclohexyl]-2-hydroxy-2-phenylacetamide; and (2S)-(1α, 5α, 6α)-6-N-[3-(4-methyl-3-pentenyl)-3-azabicyclo[3.1.0]-hexyl]-2-[(1R or 1S, 3R or 3S)-3-fluorocyclopentyl]-2-hydroxy-2-phenylacetamide.

6. A pharmaceutical composition comprising a therapeutically effective amount of a compound as defined in any one of claims 1-5 together with pharmaceutically acceptable carriers, excipients or diluents.

7. A method for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorder (COPD), pulmonary fibrosis, irritable bowel syndrome, obesity, diabetes and gastrointestinal hyperkinesis, comprising administering to said animal or human, a therapeutically effective amount of a compound having the structure of Formula I, Formula I

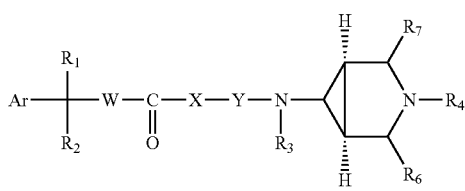

and its pharmaceutically acceptable salts, pharmaceutically acceptable enantiomers, diastereomers, N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhalo-alkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents alkyl, $C_3$-$C_7$ cycloalkyl ring in which any 1-4 hydrogen atoms are substituted with halogen (e.g. F, Cl, Br, I), carbamoyl or lower alkyl;

W represents $(CH_2)_p$, where p represents 0 to 1;

X represents an oxygen, sulphur, NR or no atom wherein R represents hydrogen or $C_1$-$C_6$ alkyl;

Y represents $CHR_5CO$ wherein $R_5$ represents hydrogen, methyl or $(CH_2)q$ wherein q represents 0 to 4;

$R_3$ represents hydrogen, lower alkyl or $CO_2C(CH_3)_3$;

$R_6$ and $R_7$ are independently selected from H, lower alkyl, COOH, $CONH_2$, $NH_2$, $CH_2NH_2$; and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$).

8. The method according to claim 7 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorder (COPD), pulmonary fibrosis, irritable bowel syndrome, obesity, diabetes and gastrointestinal hyperkinesis, comprising administering to said animal or human, a therapeutically effective amount of a compound having the structure of Formula II and its pharmaceutically acceptable salts, pharmaceutically acceptable enantiomers, diastereomers, or N-oxides, wherein Ar, $R_1$, $R_2$, W, X, Y, $R_3$ and $R_4$ are as defined for Formula I, Formula II

9. The method according to claim 7 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorder (COPD), pulmonary fibrosis, irritable bowel syndrome, obesity, diabetes and gastrointestina hyperkinesis, comprising administering to said animal or human, a therapeutically effective amount of a compound having the structure of Formula III and its pharmaceutically acceptable salts, pharmaceutically acceptable enantiomers, diastereomers, or N-oxides, wherein Ar, $R_1$, $R_2$, $R_3$ and $R_4$ are as defined for Formula I,

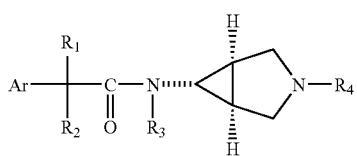

Formula-III

10. The method according to claim 7 for treatment of an animal or a human suffering from a disease or disorder of the respiratory, urinary and gastrointestinal systems, wherein the disease or disorder is urinary incontinence, lower urinary tract symptoms (LUTS), bronchial asthma, chronic obstructive pulmonary disorder (COPD), pulmonary fibrosis, irritable bowel syndrome, obesity, diabetes and gastrointestina hyperkinesis, comprising administering to said animal or human, a therapeutically effective amount of a compound having the structure of Formula-IV and its pharmaceutically acceptable salts, pharmaceutically acceptable enantiomers, diastereomers, or N-oxides, wherein $R_3$ and $R_4$ are as defined for Formula I, s represents 1to 2, $R_9$=H or F, and $R_{10}$=F,

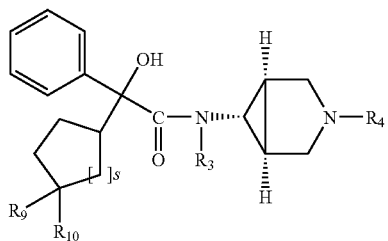

Formula IV

11. The method for treatment of an animal or a human suffering from a disease or disorder of the respiratory, urinary and gastrointestinal systems, wherein the disease or disorder is selected from urinary incontinence, lower urinary tract symptoms (LUTS), bronchial asthma, chronic obstructive pulmonary disorders (COPD), pulmonary fibrosis, irritable bowel syndrome, obesity, diabetes and gastrointestina hyperkinesis, comprising administering to said animal or human, a therapeutically effective amount of the pharmaceutical composition according to claim 6.

12. A process of preparing compounds of Formula I,

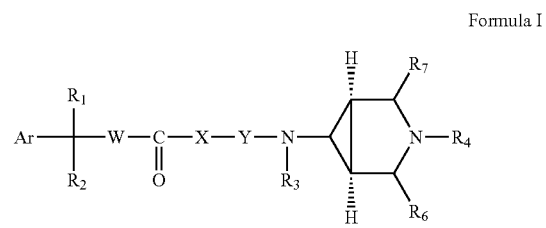

Formula I and their pharmaceutically acceptable salts, pharmaceutically acceptable enantiomers, diastereomers, or N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhaloalkyl ($C_1$-$C_4$), cyano, hydroxy, nitro, halogen (e.g. F, Cl, Br, I), lower alkoxy ($C_1$-$C_4$), lower perhalo-alkoxy ($C_1$-$C_4$), unsubstituted amino, N-lower alkylamino ($C_1$-$C_4$) or N-lower alkylamino carbonyl ($C_1$-$C_4$);

$R_1$ represents a hydrogen, hydroxy, hydroxymethyl, amino, alkoxy, carbamoyl or halogen (e.g. fluorine, chlorine, bromine and iodine);

$R_2$ represents alkyl, $C_3$-$C_7$ cycloalkyl ring in which any 1-4 hydrogen atoms are substituted with halogen (e.g. F, Cl, Br, I), carbamoyl or lower alkyl;

W represents $(CH_2)_p$, where p represents 0 to 1;

X represents an oxygen, sulphur, NR or no atom wherein R represents hydrogen or $C_1$-$C_6$ alkyl;

Y represents $CHR_5CO$ wherein $R_5$ represents hydrogen, methyl or $(CH_2)q$ wherein q represents 0 to 4;

$R_3$ represents hydrogen, lower alkyl or $CO_2C(CH_3)_3$;

$R_6$ and $R_7$ are independently selected from H, lower alkyl, COOH, $CONH_2$, $NH_2$, $CH_2NH_2$; and $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$), comprising (a) condensing a compound of Formula VI with a compound of Formula V

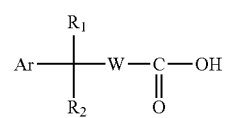

Formula VI

-continued

Formula V

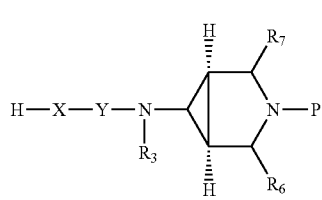

wherein Ar, $R_1$, $R_2$, W, X, Y, $R_3$, $R_6$ and $R_7$ are as defined earlier for Formula I, to give a protected compound of Formula VII wherein Ar, $R_1$, $R_2$, W, X, Y, $R_3$, $R_6$ and $R_7$ are as defined earlier and P is a protecting group for an amino group, Formula VII

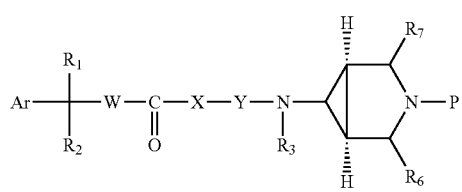

deprotecting the compound of Formula VII in the presence of a deprotecting agent to give an unprotected compound of Formula VIII wherein Ar, $R_1$, $R_2$, $R_3$, W, X, Y, $R_3$, $R_6$ and $R_7$ are as defined earlier, and Formula VIII

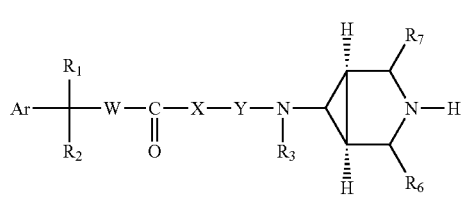

(b) N-alkylated or benzylated the compound of Formula VIII with a suitable alkylating or benzylating agent to give compounds of Formula I wherein Ar, $R_1$, $R_2$, W, X, Y, $R_3$, $R_4$, $R_6$ and $R_7$ are as defined earlier.

13. A process of preparing compounds of Formula IV,

Formula IV

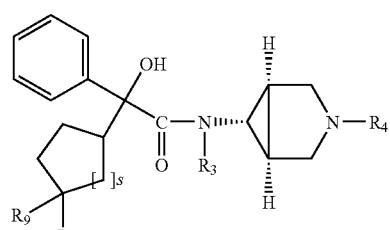

and their pharmaceutically acceptable salts, pharmaceutically acceptable enantiomers, diastereomers, or N-oxides, wherein $R_3$ represents hydrogen, lower alkyl or $CO_2C(CH_3)_3$; $R_4$ represents $C_1$-$C_{15}$ saturated or unsaturated aliphatic hydrocarbon (straight chain or branched) in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, heteroarylalkenyl group may be substituted with lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$); s represents 1 to 2, $R_9$ is H or F and $R_{10}$ is F, comprising (a) condensing a compound of Formula IX with a compound of Formula X Formula IX

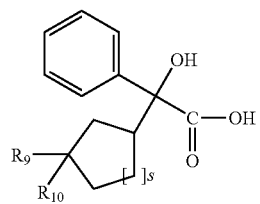

Formula X

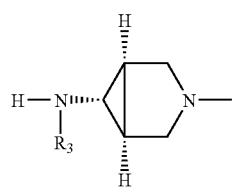

wherein $R_3$ and $R_4$ are as defined earlier for Formula I, s represents 1 to 2, $R_9$ is H or F and $R_{10}$ is F, to give a protected compound of Formula XI wherein $R_3$, $R_4$, s, $R_9$ and $R_{10}$ are as defined earlier and P is a protecting group for an amino group,

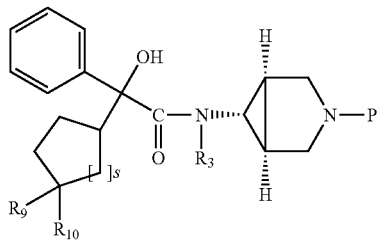

Formula XI (b) deprotecting the compound of Formula XI in the presence of a deprotecting agent to give an unprotected compound of Formula XII wherein $R_3$, $R_4$, s, $R_9$ and $R_{10}$ are as defined earlier, and

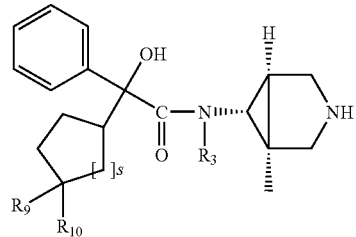

Formula XII (c) N-alkylated or benzylated the compound of Formula XII with a suitable alkylating or benzylating agent to give compounds of Formula IV wherein $R_3$, $R_4$, s, $R_9$ and $R_{10}$ are as defined earlier.

* * * * *